United States Patent [19]
House et al.

[11] Patent Number: 6,029,504
[45] Date of Patent: Feb. 29, 2000

[54] TUBE LOADING APPARATUS

[75] Inventors: Philip Edward House, East Windsor, Conn.; Alan Brian Goulet, Springfield, Mass.

[73] Assignee: ABB Combustion Engineering Nuclear Power, Inc., Windsor, Conn.

[21] Appl. No.: 09/108,119

[22] Filed: Jul. 1, 1998

[51] Int. Cl.[7] ............................... G01N 3/06; F24H 9/16
[52] U.S. Cl. ............................... 73/40; 73/49.5; 73/49.1; 73/790; 73/796; 165/499; 165/DIG. 8
[58] Field of Search ............... 73/40, 49.5, 40.5 R, 73/49.1, 790, 796, 865.6; 165/DIG. 8, DIG. 470, DIG. 471, DIG. 477, DIG. 478, DIG. 499, DIG. 492, DIG. 480, 11.1

[56] References Cited

U.S. PATENT DOCUMENTS

| | | | |
|---|---|---|---|
| 4,072,183 | 2/1978 | Fraas | 165/11 |
| 4,513,903 | 4/1985 | Feldstein et al. | 228/107 |
| 4,574,618 | 3/1986 | Anthony et al. | 73/40.5 R |
| 4,822,176 | 4/1989 | Daum | 374/57 |
| 5,158,162 | 10/1992 | Fink et al. | 188/378 |
| 5,438,862 | 8/1995 | Keating et al. | 73/49.2 |
| 5,611,948 | 3/1997 | Hawkins | 219/121.63 |

*Primary Examiner*—Hezron Williams
*Assistant Examiner*—J. David Wiggins
*Attorney, Agent, or Firm*—Rader, Fishman & Grauer; Ronald P. Kananen

[57] ABSTRACT

A tube loading apparatus and method for tensile strength and leak testing an elongated, hollow tube such as a steam generator heat transfer tube of a steam generator plant. The apparatus may be used to determine the axial or compressive load placed on a hollow tube. The tube loading apparatus includes a pair of spaced apart, plates oriented parallel to one another; at least two elongated connecting members extending between the plates in a parallel direction relative to one another, wherein each elongated connecting member is carried by each plate comprising the pair of plates and is received in a corresponding pair of openings formed in the pair of plates for each elongated member; at least two load inducing devices for imparting an axial or compressive load to the pair of plates, wherein the load inducing devices are carried by the elongated members; a load measuring device carried by one of the pair of plates for measuring the load induced in the pair of plates; and a load counterbalancing device carried by the other plate of the pair of plates, wherein the load counterbalancing device imparts an axial compressive load along said other plate. Each element of the tube loading apparatus may be constructed of stainless steel.

9 Claims, 3 Drawing Sheets

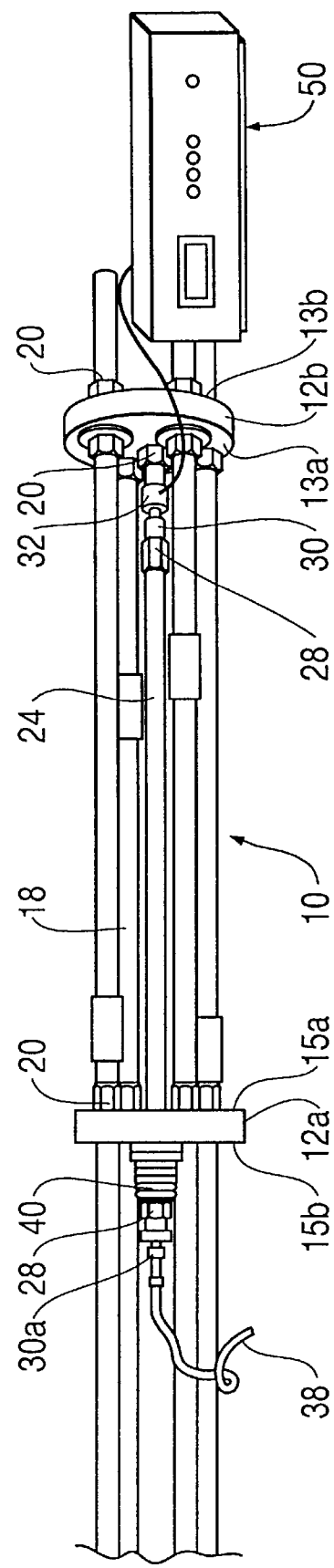

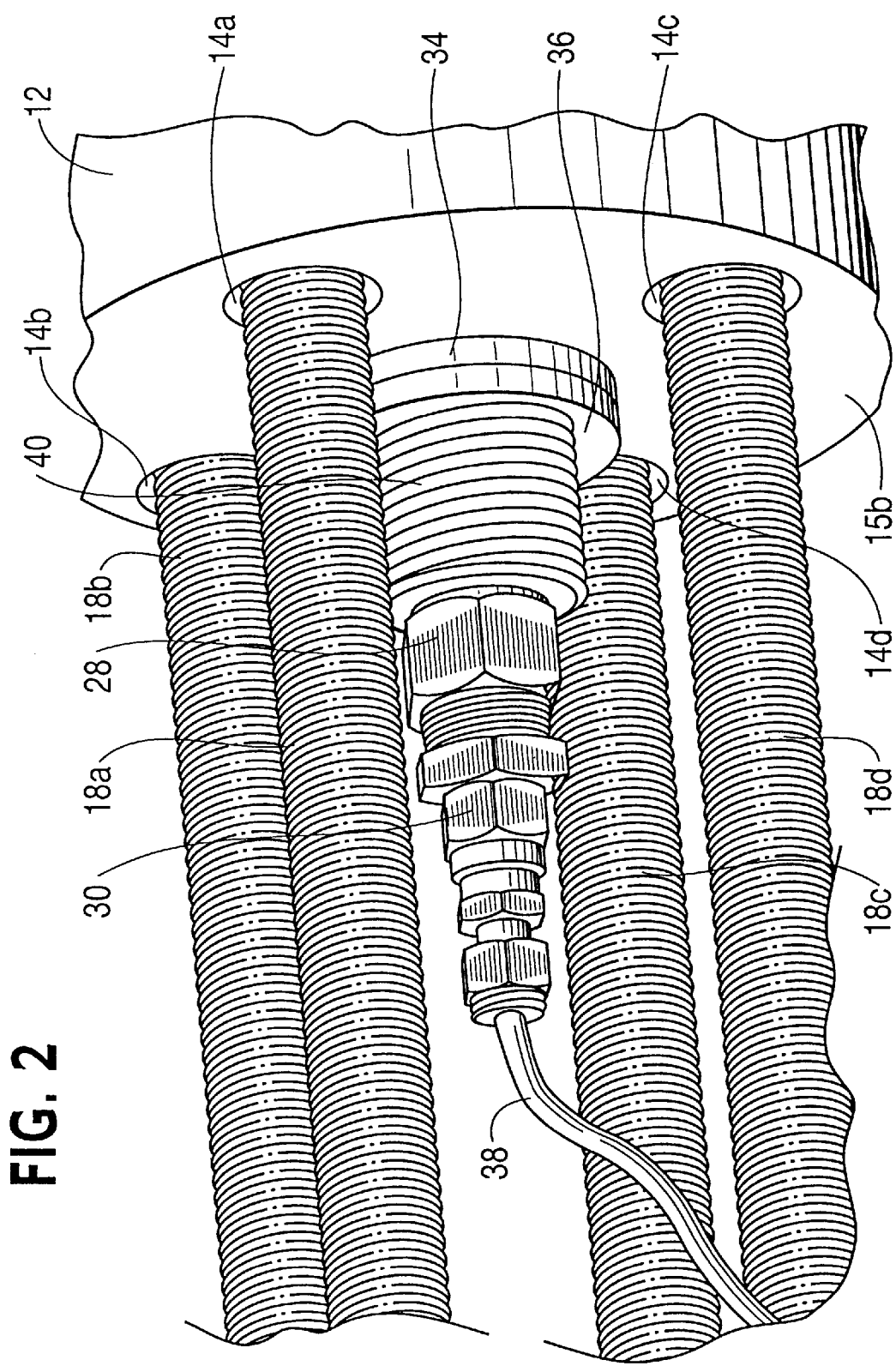

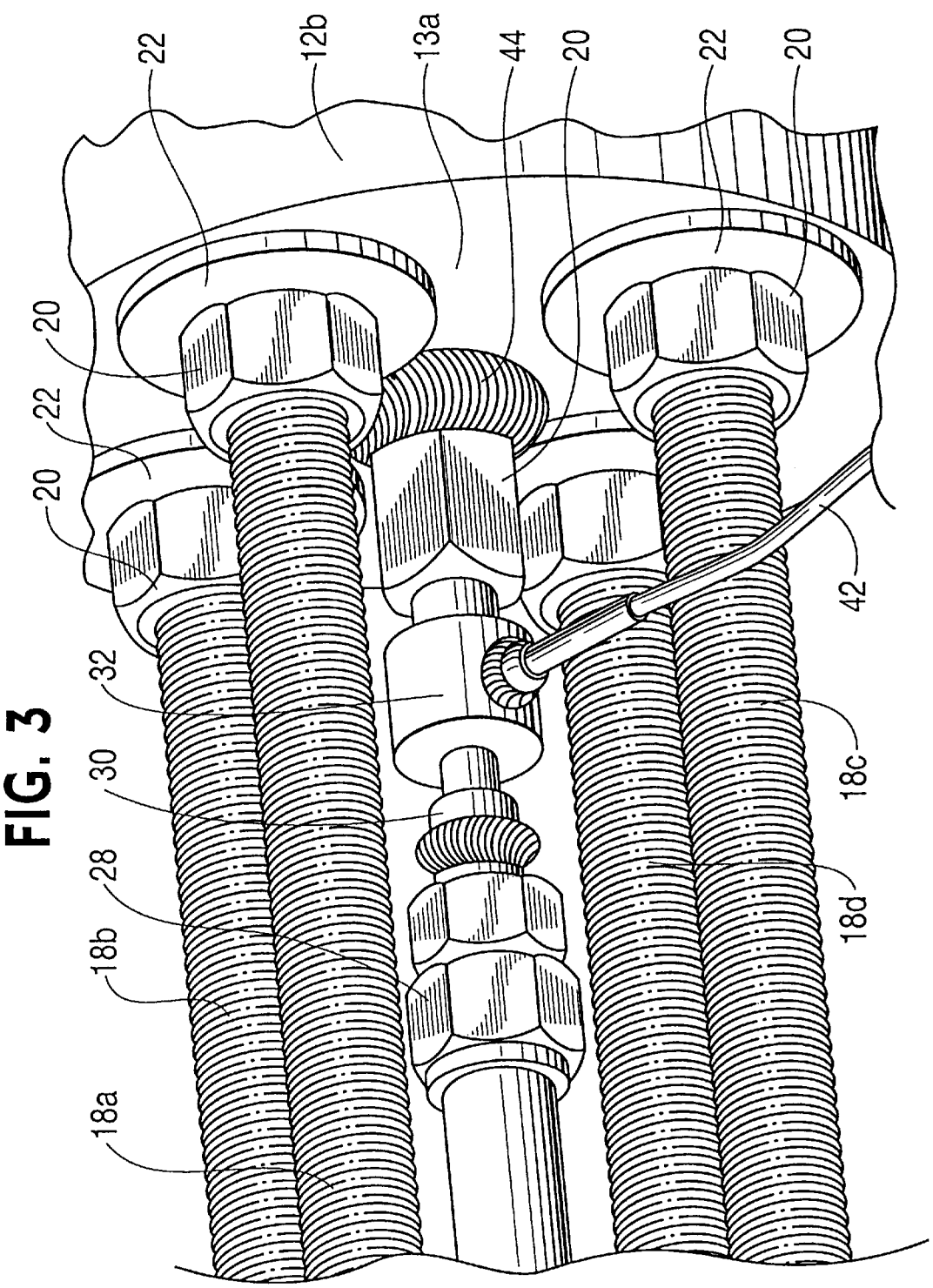

TUBE LOADING APPARATUS

FIELD OF THE INVENTION

The present invention relates generally to an apparatus and method for loading and leak testing an elongated hollow member. More particularly, the invention relates to an apparatus and method for axially loading a steam generator tube and pressure testing the tube for leaks.

BACKGROUND OF THE INVENTION

Conventional tube loading machines may be used to introduce an axially oriented tensile load onto a steam generator tube section. To test the tensile strength of the tube, the tube is simply loaded into the tube section of a tensile strength testing apparatus. However, such machines are not capable of simultaneously measuring the tensile strength and testing the tube under pressure for leaks. Hence, an apparatus is needed that would permit simultaneous tensile and leak testing of an elongated hollow tubular member.

SUMMARY OF THE INVENTION

The present invention is directed to a tube loading apparatus and method for axially loading and testing the tube under pressure for leaks. The tube loading apparatus includes a pair of plates, at least two elongated connecting members, a load inducing device, a load measuring device, and a load counterbalancing device. Each element of the tube loading apparatus may be constructed of stainless steel.

When the tube loading apparatus is assembled, the plates are spaced apart and extend in a direction parallel to one another. The elongated connecting members also extend parallel to one another, and each elongated connecting member extends between the plates such that each elongated connecting member is carried by each plate comprising the pair of plates. Additionally, each elongated connecting member supports at least one load inducing device. The load inducing device imparts either an axial tensile or compressive load onto the plates. This induced load is measured by the load measuring device, which is carried by one plate of the pair of plates. The other plate of the pair of plates supports the load counterbalancing device. The load counterbalancing device imparts an axial compressive load along said other plate.

In operation, the plates support each elongated connecting member such that the plates may be forced toward or away from one another by the load inducing device. As the plates are secured a substantially fixed position along the elongated connecting members, forcing the plates toward or away from one another sets up either a compressive or tensile load in the plates. As will be discussed below, this induced load is transferred to the tube to be tested.

The tube to be tested may be a hollow, elongated steam generator-type tube. The tube is positioned between and supported by the pair of plates. The tube extends between the plates in a direction parallel to that of the elongated connecting members. Each end of the tube is fitted with a tube end cap and fitting, wherein one fitting is configured to permit filling the tube with a liquid.

Under one testing scenario, the tube is filled with a liquid and pressurized to determine the existence of leaks therein. Simultaneously, a tensile load is applied to one or both plates, thus, forcing the plates in a direction away from one another. This action creates an axial tensile load on the plates and the tube, as the axial or compressive force induced in the plates is transferred to the tube. This axial force is measured by the load measuring device. Under a second scenario, a compressive load is applied to either one or both of the plates, thus forcing the plates toward one another. This compressive load is measured using the load measuring device. Again, the tube is simultaneously filled with a liquid and pressurized to determine the existence of leaks therein.

BRIEF DESCRIPTION OF THE DRAWINGS

The features and inventive aspect of the present invention will become more apparent upon reading the following detailed description, claims and drawing, of which the following is a brief description:

FIG. 1 is a perspective view showing a tube loading apparatus formed in accordance with the teachings of the present invention.

FIG. 2 is a detail view showing the spring loaded washer incorporated in the tube loading apparatus shown in FIG. 1.

FIG. 3 is a detail view showing the load measuring device incorporated in the tube loading apparatus shown in FIG. 1.

DESCRIPTION OF THE PREFERRED EMBODIMENT

FIG. 1 shows a preferred embodiment of a tube loading apparatus 10. Constituent components of the apparatus 10 include a pair of plates 12a, 12b, at least two elongated connecting members 18, a load measuring device 32, and a load counterbalancing device 40, and nuts 20 that serve as coupling devices for the elongated connecting members 18 and the plates 12a, 12b, and can also serve as load inducing devices.

The plates 12a, 12b are spaced apart and extend parallel relative to one another. Each plate 12a, 2b defines openings 14 and a central opening (not shown) disposed between the openings 14. In the preferred embodiment, the openings 14 are located in corresponding locations on each of the plates 12a, 12b. The openings 14 may be arranged in a rectangular or square pattern such that two openings are placed above and below the central opening. The plate 12b includes a welded joint 44 carried by the inside surface 13a. The plate 12a includes a load bearing surface 36 extending outwardly from the outside surface 15b of the plate 12a.

The plates 12a, 12b have a circular configuration. However, one of ordinary skill in the art will appreciate that the plates 12a, 12b may be configured using a variety of shapes and configurations. In the preferred embodiment, the plates are constructed of stainless steel. However, other materials having similar mechanical properties may be used.

The elongated connecting members 18 mechanically couple the plates 12a, 12b together. The apparatus 10 may include at least two elongated connecting members 18 for imparting an axial or compressive load onto the plates 12a, 12b. The preferred embodiment includes four elongated connecting members 18a, 18b, 18c, 18d constructed of a stainless steel material. However, the elongated connecting members may comprise any material having similar mechanical properties, and may comprise any suitable shape and configuration that will permit slight movement of one plate relative to the other.

As shown in FIG. 1, the elongated connecting members 18 extend between the plates 12a, 12b in a direction parallel to one another. As illustrated in FIG. 2, the elongated connecting members 18 extend substantially perpendicularly to the plates 12a, 12b such that each elongated connecting member 18 is received in a pair of corresponding openings 14a, 14b, 14c, 14d defined by plates 12a, 12b. For example, the elongated connecting member 18a is received in the pair of corresponding openings 14a formed in plates 12a, 12b. The remaining elongated connecting members 18b, 18c, 18d, are received in the pair of corresponding openings 14b, 14c, 14d. A portion of each elongated connecting member 18 may extend beyond the openings 14.

Ordinary fastening means couple the elongated connecting members 18 to the plates 12a, 12b. In the preferred embodiment, the fastening means is a nut 20 and washer 22 combination. At plate 12b, one nut 20 and washer 22 pair is threaded onto the elongated connecting member 18 such that one nut 20 and washer 22 combination is carried by both the inside and outside faces 13a, 13b. Thus, plate 12b is substantially fixed in position along the elongated connecting member 18. At plate 12a, one nut 20 and washer 22 combination is threaded onto the elongated connecting member 18 and carried by the inside face 15a of plate 12a. This coupling arrangement permits slight movement of both the plates 12a, 12b when axially loaded as discussed below.

In a preferred embodiment, the nuts 20 can serve as load inducing devices. When the load inducing devices 20 are rotated, the plates 12a, 12b may be forced away or toward one another. Depending on the direction of the force placed on the plates 12a, 12b, either a compressive or tensile force is imparted thereto. When the hexagonal nuts 20 are turned and caused to move along the elongated connecting member 18, the plates 12a, 12b are either forced toward or away from one another. When the hexagonal nut is rotated such that the plates 12a, 12b move away from one another, an axial tensile load develops in the plates 12a, 12b. As discussed below, this load is transferred to the hollow, elongated tube being tested.

The load measuring device 32 measures the magnitude of the compressive or tensile load induced in the plates 12a, 12b. The load measuring device 32 is carried by the inside face 13a of the plate 12b. However, one skilled in the art will appreciate that the load measuring device 26 may be placed on either the inside face 13a or the outside face 13b of plate 12b. As shown in FIGS. 1 and 2, the load measuring device is supported by a welded joint 44 carried by the plate 12b. The load measuring device 32 may be any conventional device known in the art for measuring a load placed on a load bearing surface. For example, in the preferred embodiment, the load measuring device 32 is a strain gage type transducer of the type commonly known in the art. As shown in FIG. 1, the transducer is connected to a voltmeter 50 by the lead wire 42 for reading the load placed on the plate 12b in terms of the voltage level shown at the transducer.

The load counterbalancing device 40 is carried by the outside face 15b of plate 12a. The load counterbalancing device 40 imparts a uniformly distributed force that acts against the load bearing surface 36. In the preferred embodiment, the load counterbalancing device 40 is a plurality of spring loaded washers.

As discussed above the plates 12a, 12b are spaced apart and extend parallel to one another. The plate 12b supports the load measuring device 32, and the plate 12a supports the load counterbalancing device 40. Each elongated connecting member 18 extends between and is supported by the plates 12a, 12b, and a nut 20 and washer 22 combination couples the plates to the elongated connecting members 18.

The tube 24 to be tested is positioned between the plates 12a, 12b. The tube 24 and the elongated connecting members 18 extend in the same direction between the plates 12a, 12b. Each end of the tube 24 is received in the openings 16 defined by the plates 12a, 12b. The tube 24 is capped on one end by a conventional tube end cap 28 and tube fitting 30. The other end of the tube 24 is capped by a similar tube end cap 28a and tube fitting 30a. The fitting 30a is configured to permit filling the tube 24 with a liquid such as water distilled water or any other suitable substance. As shown in FIG. 2, the fitting 30a includes a connecting line 38 through which fluid may enter and exit the tube 24. The tube end caps 28, 28a and fittings 30, 30a are conventional devices commonly known in the art. For example, the preferred embodiment includes Swagelok™ end caps.

At one end, the tube 24 is coupled to the load measuring device 32. At the opposite end, the tube 24 is held in virtually a fixed position using a lock washer 34. The lock washer 34 is located between the load counterbalancing device 40 and the bearing surface 36 formed at plate 12a. The load counterbalancing device 40 is positioned on the tube 24 between the load bearing surface 36 and the end cap 28.

The load inducing devices 20, hexagonal nuts, are rotated until the desired axial load is placed on the tube 24, the load being measured by the load measuring device 32.

When the tube 24 is filled with a liquid and pressurized, the tube 24 may lengthen due to the internal pressure of the tube 24. To prevent the tube 24 from lengthening during leak testing, the load counterbalancing device 40 imparts a constant, opposing force against the bearing surface 36. This compressive force is uniformly distributed around the circumference of the tube 24.

The disclosed embodiment is given to illustrate the invention. However, it is not intended to limit the scope and spirit of the invention, as a variety of configurations which may be employed to fabricate the tube loading apparatus 10. Therefore, the invention should be limited only by the appended claims.

We claim:

1. A tube loading apparatus for receiving an elongated hollow tube during axial load testing or fluid leak testing, comprising:

a pair of spaced apart plates extending parallel to one another, each plate having at least a central opening for receiving said elongated hollow tube during axial load testing or fluid leak testing;

at least two elongated connecting members extending in a parallel direction between the pair of plates, wherein the elongated connecting members are each supported by each plate of the pair of plates;

at least two load inducing devices for imparting a mechanical force load to the pair of plates, the load inducing device being carried by the elongated connecting member;

a load measuring device carried by one of the pair of plates for measuring the axial load that includes an axial tensile load or an axial compressive load induced on the pair of plates; and a load counterbalancing device carried by the other plate of the pair of plates, the load counterbalancing device imparting a compressive load on said other plate.

2. The tube loading apparatus as defined in claim 1, wherein each of the pair of plates comprised of stainless steel.

3. The tube loading apparatus as defined in claim 1, wherein an elongated, hollow tube is positioned between the pair of plates and extends in the same direction as the elongated connecting members, the tube being fitted on each end with a tube end cap and fitting, wherein one fitting is configured to permit water to enter the tube.

4. The tube loading apparatus as defined in claim 3, wherein the plates forming the pair of plates are forced in a direction away from one another, resulting in an axial tensile load being induced onto the tube, wherein the axial tensile load is measured by the tube measuring device.

5. The tube loading apparatus as defined in claim 4, wherein the tube is filled with a liquid and tested for leaks.

6. A tube loading apparatus use in load testing steam generator tubes, comprising:

a pair of spaced apart steel plates extending parallel to one another, each plate of said pair of plates defining four first openings and a second central opening for receiving an elongated hollow tube during axial load testing or fluid leak testing, wherein the first openings are formed in corresponding positions on each plate of the pair of plates;

four threaded rods extending between the plates in a parallel direction relative to one another, wherein the rods extend substantially perpendicularly to plates and are each received in a corresponding pair of first openings formed in the pair of plates;

a transducer for measuring an axial load that includes an axial tensile load or an axial compressive load placed on the plates forming the pair of plates, the transducer being carried by one plate of said pair of plates;

four nuts, wherein one nut is carried by each of the threaded rods for inducing the axial tensile load to the loading apparatus; and at least one spring loaded washer carried by the other plate of said pair of plates for providing an axial compressive force against said other plate.

7. The tube loading apparatus as defined in claim 6, wherein said elongated, hollow tube is positioned between the pair of plates and received in the second opening, said tube extending in the same direction as the elongated connecting member, said tube further being fitted on each end with a tube end cap and fitting, wherein one fitting is configured to permit water to enter the tube.

8. The tube loading apparatus as defined in claim 7, wherein the tube is filled with a liquid and tested for leaks.

9. A method for mechanical force loading a steam generation tube for use in load testing, comprising:

providing two spaced apart plates extending parallel relative to one another, said plates having at least a central opening for receiving an elongated, hollow tube;

extending at least two elongated connecting members in a parallel direction between the two plates, wherein the elongated connecting members each extend substantially perpendicularly to the two plates, said elongated connecting member further being carried by the two plates;

placing said elongated, hollow tube between the two plates, wherein the tube and the elongated connecting members extend in the same direction, the tube being capped on each end using a tube end cap and fitting;

filling the tube with a liquid;

pressurizing the tube to determine the presence of leaks in the tube;

imparting a counterbalancing load on the tube to prevent the tube from lengthening under pressure;

inducing an axial load on the tube, while maintaining the tube under pressure; and measuring the induced axial load that includes an axial tensile load or an axial compressive load.

* * * * *